United States Patent [19]

Wittle et al.

[11] 4,043,994

[45] Aug. 23, 1977

[54] NEW PENTAPEPTIDES AND METHODS FOR THEIR PRODUCTION

[75] Inventors: Eugene Leroy Wittle; Ernest D. Nicolaides, both of Ann Arbor; Marland Paul Hutt, Saline, all of Mich.

[73] Assignee: Parke, Davis & Company, Detroit, Mich.

[21] Appl. No.: 699,125

[22] Filed: June 23, 1976

[51] Int. Cl.$^2$ ............................................. C07C 103/52
[52] U.S. Cl. .................... 260/112.5 LH; 260/112.5 R; 424/177
[58] Field of Search ............... 260/112.5 LH, 112.5 R

[56] References Cited

U.S. PATENT DOCUMENTS 3,796,697  3/1974  Flouret ..................... 260/112.5 LH

OTHER PUBLICATIONS

Biochem. and Biophys. Res. Comm. (1974) 57, 1248-1256.
Biochem. and Biophys. Res. Comm. (1974) 60, 406-412.

*Primary Examiner*—Delbert R. Phillips
*Attorney, Agent, or Firm*—Stephen Raines; David B. Ehrlinger; George M. Richards

[57] ABSTRACT

New pentapeptides having the formula X-R-Ser-(benzyl)-Tyr(benzyl)-R$^1$-Y wherein X is t-butoxycarbonyl or benzyloxycarbonyl, R is a single amino acid fragment or a dipeptide fragment utilizing amino acids selected from the group consisting of Aze, His(benzyl) and Trp; R$^1$ is a single amino acid fragment or a dipeptide fragment utilizing amino acids selected from the group consisting of Ala, Leu and Pro and Y is lower alkoxy, hydrazino, amino, lower alkylamino or di(lower alkyl)amino with the priviso that the total number of amino acid units when R and R$^1$ are combined is three.

7 Claims, No Drawings

NEW PENTAPEPTIDES AND METHODS FOR THEIR PRODUCTION

SUMMARY AND DETAILED DESCRIPTION

The present invention relates to new peptide compounds that are useful luteinizing hormone releasing factor antagonists and to methods for their production. More particular, the invention relates to new N-protected pentapeptides that are represented by the formula $$\text{X—R—Ser(benzyl)—Tyr(benzyl)—R}^1\text{—Y} \qquad \text{I}$$

wherein X is t-butoxycarbonyl or benzyloxycarbonyl, R is a single amino acid fragment or a dipeptide fragment utilizing amino acids selected from the group consisting of Aze, His(benzyl) and Trp; $R^1$ is a single amino acid fragment or a dipeptide fragment utilizing amino acids selected from the group consisting of Ala, Leu and Pro and Y is lower alkoxy, hydrazino, amino, lower alkylamino or di(lower alkyl)amino with the proviso that the total number of amino acid units when R and $R^1$ are combined is three.

The preferred compounds of formula I are those wherein X is t-butoxycarbonyl, R is Trp or His(benzyl), $R^1$ is Ala-Leu or Ala-Pro and Y is methoxy or ethylamino.

In formula I, the conventional symbols for amino acid residues of peptide compounds linked thereto are used and each is intended to have the following meaning: Pro, D-prolyl or L-prolyl; Aze, D-2-azetidinylcarbonyl or L-2-azetidinylcarbonyl; His(benzyl), $N^{im}$-benzyl-D-histidyl or $N^{im}$-benzyl-L-histidyl; Trp, D-tryptophyl or L-tryptophyl; Ala, D-alanyl or L-alanyl; Try(methyl), D-tyrosyl(methyl) or L-tyrosyl(methyl) and Ser(benzyl), D-seryl(benzyl) or L-seryl(benzyl). In addition, the term "lower alkyl" is intended to mean a straight, branched or cyclic hydrocarbon moiety of up to six carbon atoms, such as methyl, ethyl, isopropyl and cyclopropyl and "lower alkoxy" is intended to mean an alkoxy group having a straight, branched or cyclic hydrocarbon moiety of up to six carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein X, R and $R^1$ are as previously defined and Y is lower alkoxy, are produced by removing a protected pentapeptide from a resin complex of the following structure $$\text{X—R—Ser(benzyl)—Tyr(benzyl)—R}^1\text{-resin} \qquad \text{II}$$

wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected pentapeptide through a methyleneoxy bridge wherein the methylene group is attached to the polymeric portion of the resin and the oxygen atom is attached to the protected pentapeptide and X, R and $R_1$ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein Y is hydrazino, amino, lower alkylamino or di(lower alkyl)amino may be prepared by reacting compounds of the formula II wherein X, R and $R^1$ are as previously defined, with hydrazine, ammonia, lower alkylamine or di(lower alkyl)amine.

The resin complex is suspended in a solvent, such as methanol, ethanol, dimethylformamide, etc., at a temperature of from about 0° to 50° C. for periods of from 12 hours to 10 days. When employing less reactive amines, the preferred solvent is dimethylformamide.

The complex resins of the formula II are prepared by coupling a protected amino acid of the formula $$\text{X—R—OH} \qquad \text{III}$$

wherein X is as previously defined and R is Aze, His(benzyl) or Trp with complex resins of the formula $$R^2\text{—Ser(benzyl)-Tyr(benzyl)—R}^1\text{—resin} \qquad \text{IV}$$

wherein $R^1$ is as described in formula I and $R^2$ is hydrogen, Aze, His(benzyl) or Trp with the proviso that the total number of amino acid units when $R^1$ and $R^2$ are combined is two, in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about 15 minutes to about 20 hours.

The complex resins of the formula IV are prepared by treating complex resins of the formula $$\text{t—butoxycarbonyl—R}^2\text{—Ser(benzyl)—Tyr(benzyl-)—R}^1\text{—resin} \qquad \text{V}$$

wherein $R^1$ is as described in formula I and $R^2$ is a single bond, Aze, His(benzyl) or Trp, with the proviso that the total number of amino acid units when $R^1$ and $R^2$ are combined is two with a large excess of trifluoroacetic acid utilizing dichloromethane as the solvent at temperatures of from 20° to 30° C. for about 10 minutes followed by neutralization of the trifluoroacetic acid salt with a base such as triethylamine.

Certain of the complex resins of formula V are prepared by coupling $$\text{t-butoxycarbonyl—R}^3\text{—OH}$$

Wherein $R^3$ is Aze, His(benzyl) or Trp, to complex resins of the formula $$\text{Ser(benzyl)—Tyr(benzyl)—R}^1\text{—resin} \qquad \text{VI}$$

wherein $R^1$ is as described in formula I according to the procedure used for the preparation of compounds of formula II. More specifically, the compounds of formula V are prepared when $R^1$ is a single amino acid unit.

The complex resins of the formula VI are prepared by treating the complex resins of the formula

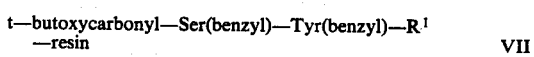    VII wherein $R^1$ is as described in formula I with trifluoroacetic acid using the reaction procedure for the preparation of compounds of the formula IV.

The complex resins of the formula VII are prepared by coupling

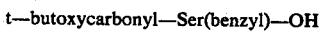

to complex resins of the formula

    VIII wherein $R^1$ is as described in formula I, according to the procedure used for the preparation of compounds of formula II.

The complex resins of the formula VIII are prepared by treating the complex resins of the formula

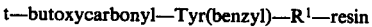    IX wherein $R^1$ is as described in formula I with trifluoroacetic acid using the reaction procedure for the preparation of compounds of the formula IV.

The complex resins of formula IX are prepared by coupling

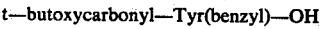

to complex resins of the formula $R^1$—resin    X wherein $R^1$ is as described in formula I according to the procedure used for the preparation of compounds of formula II.

The complex resins of the formula X are prepared by treating the complex resins of the formula t—butoxycarbonyl—$R^1$—resin    XI wherein $R^1$ is as described in formula I, with trifluoroacetic acid using the reaction procedure for the preparation of compounds of formula IV.

Certain of the complex resins of the formula XI are prepared by coupling t—butoxycarbonyl—$R^4$—OH    XII wherein $R^4$ is Ala, Leu or Pro to complex resins of the formula $R^5$—resin    XIII wherein $R^5$ is Ala, Leu or Pro, according to the procedure used for the preparation of compounds of formula II.

The complex resins of the formula XIII, which may also be used to prepare compounds of the formula XI, are prepared by treating the complex resins of the formula t—butoxycarbonyl—$R^5$—resin    XIV wherein $R^5$ is as described for formula XIII, with trifluoroacetic acid using the reaction procedure for the preparation of compounds of formula IV.

In accordance with this invention, compounds of the formula I, wherein X, R and $R^1$ are as previously described and Y is hydrazino, amino, lower alkylamino or di(lower alkyl)amino are prepared by reacting a compound of the formula I wherein Y is alkoxy, preferably methoxy, with hydrazine, ammonia, lower alkylamine or di(lower alkylamine).

The reactions are conducted at temperatures of from about 5° to 100° C. for from 3 hours to 4 days, preferably about room temperature. Generally, a large excess of amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein X, R and $R^1$ are as previously defined and Y is amino, lower alkylamino or di(lower alkyl)amino are prepared by reacting a compound of the formula

    XV with ammonia, lower alkylamine or di(lower alkyl)amine in a non-reactive solvent such as dimethylformamide, dioxane, tetrahydrofuran or mixtures thereof. The reaction is carried out at about −30° to about 0° C. for about 12 to 24 hours, preferably −20° to 0° C. for from 16 to 19 hours. The two reactants are used in approximately equimolar amounts although a slight excess of the amine, about 10 percent, is preferred. When X is t-butoxycarbonyl, care should be taken to avoid the presence of a large excess of acid.

The azide compounds of the formula XV are normally prepared in situ by reacting a peptide hydrazide of the formula

    XVI wherein X, R and $R^1$ are as defined in formula I with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° and 0° C. following the in situ formation of the azide of formula XVII and prior to the further reaction of the peptide azide with the appropriate amine to form certain pentapeptides of formula I, a tertiary amine such as triethylamine is added to the reaction mixture to neutralize the acid used.

The compounds of formula XVI are prepared by reacting a compound of formula I wherein Y is methoxy with hydrazine hydrate in methanol.

Compounds of the formula I wherein X, R and $R^1$ are as described in formula I and Y is hydrazino, amino, lower alkylamino or di(lower alkyl)amino are prepared by coupling a compound of the formula

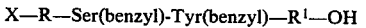    XVIII with hydrazine, ammonia, a lower alkylamine or a di(-lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula XVII are prepared by the hydrolysis of a compound of formula I wherein X, R and $R^1$ are as previously defined and Y is lower alkoxy. The reaction is conducted at temperatures of from 20° to 30° C. using about 0.5 ml. of two normal aqueous sodium hydroxide solution and 10 ml. of solvent, usually water or an alcohol such as methanol, for each millimole of ester. The compound of formula XVII is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Pentapeptides of this invention were screened for LRF antagonist activity in vitro using rat anterior pituitary cell cultures as described by Vale et. al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

ACTIVITY TABLE FOR IN VITRO TEST IN RAT ANTERIOR PITUITARY CELL CULTURES

| | Molar Conc. | LH Value ng/ml. | % LH Release Inhibition |
|---|---|---|---|
| $N^\alpha$-t-Butoxycarbonyl-D-tryptophyl-O-benzyl-L-seryl-O-benzyl-L-tyrosyl-D-alanyl-DL-proline N-ethylamide | $1 \times 10^{-6}$ | 10.61 | 84 |
| LRF Control | $2.5 \times 10^{-10}$ | 28.52 | |
| Saline Control | | 7.09 | |
| | $5 \times 10^{-6}$ | 14.02 | 90 |
| | $1 \times 10^{-6}$ | 34.51 | 43 |
| LRF Control | $5 \times 10^{-10}$ | 52.93 | |
| Saline Control | | 9.90 | |
| $N^\alpha$-t-Butoxycarbonyl-$N^{im}$-benzyl-L-histidyl-O-benzyl-L-seryl-O-benzyl-L-tyrosyl-D-alanyl-L-leucine methyl ester | $1 \times 10^{-6}$ | 20.26 | 72 |
| LRF control | $2.5 \times 10^{-10}$ | 51.62 | |
| Saline Control | | 8.32 | |
| $N^\alpha$-t-Butoxycarbonyl-$N^{im}$-benzyl-L-histidyl-O-benzyl-L-seryl-O-benzyl-L-tyrosyl-D-alanyl-L-leucyl hydrazide | $1 \times 10^{-6}$ | 19.35 | 71 |
| LRF Control | $2.5 \times 10^{-10}$ | 49.90 | |
| Saline Control | | 6.72 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511-512. Thus, the pentapeptides of this invention are useful in controlling ovulation and in restricting fertility.

The invention is illustrated by the following examples.

EXAMPLE 1

$N^\alpha$-t-Butoxycarbonyl-L-tryptophyl-O-benzyl-L-seryl-O-benzyl-L-tyrosyl-D-alanyl-L-leucine methyl ester O-Benzyl-L-seryl-O-benzyl-L-tyrosyl-D-alanyl-L-leucine methyl ester trifluoroacetic acid salt, 7 mmol is dissolved in 30 ml. of dimethylformamide, the solution cooled to −5° to 0° C. and treated with 4.2 ml. of triethylamine (pH 9). The mixture is then treated with 2.13 g. (7 mmol) of $N^\alpha$-t-butoxycarbonyl-L-tryptophan, 1 g. (7 mmol) of 1-hydroxybenztriazole and, after five minutes, with 1.6 g. of dicyclohexylcarbodiimide. The mixture is stirred for two and a half hours with ice-bath cooling and then overnight to room temperature and an additional twenty-four hours at room temperature. The mixture is filtered, the solid rinsed with dimethylformamide and the filtrate evaporated under reduced pressure. The residual oil is dissolved in 150 ml. of ethyl acetate and 200 ml. of ether and washed with 5% sodium bicarbonate solution five times (20 mls.), with saturated salt solution (20 mls.), dried over magnesium sulfate and the solvent evaporated. The residue is dissolved in 20 ml. of methanol and 100 ml. of ether and the solvents allowed to evaporate to produce a white solid which is stirred with additional ether, filtered, and dried; 5.78 g. The product is purified further by stirring in dichloromethane-ether and filtering to separate dicyclohexylurea. The filtrate is concentrated and the residue slowly crystallized from 1 ml. of methanol, ether and petroleum ether; 5 g.; m.p. 165°-168° C.

O-Benzyl-L-seryl-O-benzyl-L-tyrosyl-D-alanyl-L-leucine methyl ester trifluoroacetic acid salt is obtained by treatment of $N^\alpha$-t-butoxycarbonyl-O-benzyl-L-seryl-O-benzyl-L-tyrosyl-D-alanyl-L-leucine methyl ester, 5.23 g. (7 mmol) in 35 ml. of dichloromethane with 40 ml. of trifluoroacetic acid for ten minutes. The solution is then evaporated at 30° to 40° C. and under reduced pressure. The residual oil is solidified by treatment with 30 ml. of ether. The mixture is evaporated and the solid residue re-evaporated with 20 ml. of ether and 25 ml. of dichloromethane. The residual solid is dissolved in 30 ml. of dimethylformamide and used without further treatment.

$N^\alpha$-t-Butoxycarbonyl-O-benzyl-L-seryl-O-benzyl-L-tyrosyl-D-alanyl-L-leucine methyl ester is prepared from 10 mmoles of O-benzyl-L-tyrosyl-D-alanyl-L-leucine methyl ester is prepared from 10 mmoles of O-benzyl-L-tyrosyl-D-alanyl-L-leucine methyl ester trifluoroacetic acid salt by neutralizing to litmus with triethylamine in the cold and then adding 1.4 ml. (10 mmol) of additional triethylamine (pH 8.5). The cold solution is treated with 2.95 g. (10 mmol) of $N^\alpha$-t-butoxycarbonyl- O-benzyl-L-serine, 1.35 g. of 1-hydroxybentriazole and 2.2 g. of dicyclohexylcarbodiimide. The mixture is stirred for two and one-half hours at −5° C. and overnight at room temperature. The mixture is filtered, the solid rinsed with dimethylformamide and the filtrate evaporated at 40° C. under reduced pressure. The residue is dissolved in 50 ml. of ethyl acetate and 200 ml. of ether and washed three times with 5% sodium bicarbonate solution and with saturated salt solution, dried over magnesium sulfate and evaporated. The residue is crystallized from a minimum of methanol by adding ether; 6.6 g. The product is recrystallized from methanol-ether; 6 g.; m.p. 67°–71° C.

O-Benzyl-L-tyrosyl-D-alanyl-L-leucine methyl ester trifluoroacetic acid salt is obtained from 5.7 g. (10 mmol) of $N^\alpha$-t-butoxycarbonyl-O-benzyl-L-tyrosyl-D-alanyl-L-leucine methyl ester by dissolving in 20 ml. of dichloromethane and adding 50 ml. of trifluoroacetic acid at 25° C. The reaction is let stand for 10 minutes and the mixture evaporated to dryness under reduced pressure. The residual oil is dissolved in ether and the solvent evaporated again under reduced pressure to an oil which is used without further treatment.

$N^\alpha$-t-Butoxycarbonyl-O-benzyl-L-tyrosyl-D-alanyl-L-leucine methyl ester is prepared from 7 g. (20 mmol) of $N^\alpha$-benzyloxy-carbonyl-D-alanyl-L-leucine methyl ester by reduction with hydrogen. The material is dissolved in 150 ml. of methanol and 500 mg. of 20% palladium-on-carbon added followed by the introduction of hydrogen. The stirred reaction mixture is shown by thin layer chromatography to be complete in 2 hours. The mixture is filtered to separate the catalyst and 7.42 g. (20 mmol) of $N^\alpha$-t-butoxycarbonyl-O-benzyl-L-tyrosine added. The methanol is removed by evaporation under reduced pressure and the residue dissolved in 50 ml. of dimethylformamide. The cooled solution is treated with 2.7 g. of 1-hydroxybenztriazole and 4.3 g. of dicyclohexylcarbodiimide. The mixture is stirred at −10° C. for two hours and then at room temperature for two and one-half days. The mixture is filtered, the solid rinsed and the solvent evaporated at 40° C. under reduced pressure. The residue is dissolved in 300 ml. of ether and 50 ml. of ethyl acetate and washed three times with 5% sodium bicarbonate solution, saturated salt solution, dried over magnesium sulfate and evaporated. The residue crystallizes from ether-petroleum ether. The product is further purified by boiling with ether, cooling and filtering; 8.55 g. of white solid; m.p. 128°–129° C.

$N^\alpha$-Benzyloxycarbonyl-D-alanyl-L-leucine methyl ester is prepared from 8.92 g. (40 mmol) of $N^\alpha$-benzyloxycarbonyl-D-alanine, 7.28 g. (40 mmol) of L-leucine methyl ester hydrochloride and 5.4 g. (40 mmol) of 1-hydroxybenztriazole dissolved in 120 ml. of dimethylformamide. The solution is cooled and treated with 5.6 ml. (40 mmol) of triethylamine and then with 8.64 g. of dicyclohexylcarbodiimide. The reaction is stirred with cooling for several hours and then allowed to come to room temperature in the ice bath. It is stirred overnight at room temperature and filtered. The filtrate is evaporated at reduced pressure and the residue dissolved in 400 ml. of ethyl acetate and washed three times with 5 percent sodium bicarbonate solution, dilute hydrochloric acid, saturated salt solution, dried over magnesium sulfate and evaporated. The residue is crystallized from ether-petroleum ether, re-dissolved in ether, filtered and crystallized by addition of petroleum ether; 12.88 g.; m.p. 65°–68° C.

EXAMPLE 2

$N^\alpha$-t-Butoxycarbonyl-D-tryptophyl-O-benzyl-L-seryl-O-benzyl-L-tyrosyl-D-alanyl-DL-proline N-ethylamide $N^\alpha$-t-Butoxycarbonyl-D-tryptophyl-O-benzyl-L-seryl-O-benzyl-L-tyrosyl-D-alanyl-DL-proline methyl ester, 5 g., is treated with 10 ml. of ethylamine in methanol at room temperature for 5 days. Evaporation yields an oil which is chromatographed on silica gel using 5% methanol in benzene. The fractions are selected by thin layer chromatography, evaporated and the residue solidified with petroleum ether; white solid, 3 g.; m.p. 95°–105° C.

$N^\alpha$-t-Butoxycarbonyl-D-tryptophyl-O-benzyl-L-seryl-O-benzyl-L-tyrosyl-D-alanyl-DL-proline methyl ester is obtained by treating 13.5 g. of ethanol and ether washed, $N^\alpha$-t-butoxycarbonyl-D-tryptophyl-O-benzyl-L-seryl-O-benzyl-L-tyrosyl-D-alanyl-DL-proline resin with ten percent by volume of triethylamine in methanol for about 24 hours. The reaction mixture is filtered and the solvent evaporated to give 5 g. of an oil.

$N^\alpha$-t-Butoxycarbonyl-D-tryptophyl-O-benzyl-L-seryl-O-benzyl-L-tyrosyl-D-alanyl-DL-proline resin is obtained from 10 g. of $N^\alpha$-t-butoxycarbonyl-DL-proline resin by successive coupling according to General Procedure given below with 1) 2 g. (10.5 mmol) of $N^\alpha$-t-butoxycarbonyl-D-alanine and 1.8 g. (9 mmol) of dicyclohexylcarbodiimide, 2) 3 g. (8 mmol) of $N^\alpha$-t-butoxycarbonyl-O-benzyl-L-tyrosine and 1.8 g. of dicyclohexylcarbodiimide, 3) 2.6 g. (8.5 mmol) of $N^\alpha$-t-butoxycarbonyl-O-benzyl-L-serine and 1.8 g. of dicyclohexylcarbodiimide and 4) 2.6 g. (8.5 mmol) of $N^\alpha$-t-butoxycarbonyl-D-tryptophan and 1.8 g. of dicyclohexylcarbodiimide.

$N^\alpha$-t-Butoxycarbonyl-DL-proline resin is prepared from 50 g. of 1% chloromethylated resin, 14 g. of $N^\alpha$-t-butoxycarbonyl-DL-proline and 8.7 g. of triethylamine which are stirred together in ethanol for several days, filtered and the resin washed with ethanol, water, methanol, dichloromethane and ether. After drying, 5 g. (0.85 mmol per g.) is obtained.

GENERAL PROCEDURE FOR THE SOLID PHASE SYNTHESIS OF PEPTIDE RESINS

The peptide resin is obtained by attaching an α-amino-protected amino acid to a resin (usually a chloromethylated resin which is commercially available from Lab Systems, Inc., San Mateo, California). The peptide system is then constructed by de-protecting the α-amino-protected amino acid resin and attaching an α-amino-protected amino acid. Repetition of this process produces the peptide resin having the required number and sequence of the desired peptide. The terminal α-amino protection is changed by de-protection and attaching the desired carboxylic terminal group. The solid phase synthesis procedure is described by J. M. Stewart "Solid Phase Peptide Synthesis," W. H. Freeman and Co., 1969.

Each cycle of the procedure follows the scheme:
1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.

5. Fifteen to thirty minutes agitation with the α-amino-protected amino acid in 20% molar excess (based on the resin nitrogen analysis). In an alternate method, a 4-fold excess of the α-amino-protected amino acid is agitated with the resin for fifteen minutes and the excess recovered by draining the solution from the reactor.

6. Addition of dicyclohexylcarbodiimide at least equivalent to the α-amino-protected amino acid in Step 5 in dichloromethane followed by agitation for four to twenty hours. In the alternate method, a 3.3-fold excess of dicyclohexylcarbodiimide is used relative to the α-amino-protected amino acid resin.

7. Three washes with dichloromethane.

EXAMPLE 3:

N$^\alpha$-t-Butoxycarbonyl-N$^{im}$-benzyl-L-histidyl-O-benzyl-L-seryl-O-benzyl-L-tyrosyl-D-alanyl-L-leucine methyl ester N$^\alpha$-t-Butoxycarbonyl-O-benzyl-L-seryl-O-benzyl-L-tyrosyl-D-alanyl-L-leucine methyl ester, 5.23 g. (7 mmol) is converted to O-benzyl-L-seryl-O-benzyl-L-tyrosyl-D-alanyl-L-leucine methyl ester trifluoroacetic acid salt (Example 1). The residual oil is dissolved in 30 ml. of dimethylformamide, cooled to −5° C. and treated with triethylamine to pH 9. The cold solution is then treated with 2.42 g. (7 mmol) of N$^\alpha$-t-butoxycarbonyl-N$^{im}$-benzyl-L-histidine, 1 g. (7 mmol) of 1-hydroxybenztriazole, stirred at −5° C. and treated with 1.6 g. (7 mmol) of dicyclohexylcarbodiimide. The mixture is stirred for several hours in the cold and then overnight at 20° C. It is then filtered and the filtrate evaporated under reduced pressure. The residue is treated with 75 ml. of methanol and filtered. Evaporation of the methanol filtrate yields an oil which is dissolved in ether containing a small amount of methanol and washed with 10% sodium bicarbonate solution and then with water. The ether is separated and dried over magnesium sulfate, filtered and evaporated to a solid which is washed with a small quantity of ether followed by a small quantity of methanol; 1.75 g. The product is further purified by stirring with 7 ml. of methanol, adding 20 ml. of dry ether and concentrating, adding ether and allowing further evaporation on standing. The solid appears as ether increases and methanol decreases. The mixture is filtered and the solid washed with ether; 1.19 g. with 1 CH$_3$OH of solvation; m.p. 147°–150° C.

EXAMPLE 4:

N$^\alpha$-t-Butoxycarbonyl-N$^{im}$-benzyl-L-histidyl-O-benzyl-L-seryl-O-benzyl-L-tyrosyl-D-alanyl-L-leucyl hydrazide The methyl ester of Example 3, as an oil, 4.66 g., is dissolved in methanol and treated with an excess of hydrazine hydrate at room temperature. The solution, after reacting overnight, is filtered and evaporated. The residue is taken into methanol and again evaporated The residue is taken into a small amount of methanol, filtered and the solution dropped into ethyl acetate and ether to yield a white solid; 870 mg.; m.p. 75°–80° C. Further material is obtained from the solution by evaporation and repeated precipitation of the residue from methanol with ethyl acetate and ether; 1.5 g.; m.p. 72°–75° C. The material is further purified by dissolving in chloroform and ether containing a small quantity of methanol. The solution is washed with 5% sodium bicarbonate solution and with water, dried over magnesium sulfate and evaporated. The residue crystallizes in ether-methanol. Repeated treatment with methanol-ether yields 580 mg.; m.p. 98°–102° C.

EXAMPLE 5:

N$^\alpha$-Benzyloxycarbonyl-D-2-azetidinylcarbonyl-N$^{im}$-benzyl-L-histidyl-O-benzyl-L-seryl-O-benzyl-L-tyrosyl-D-alanine methyl ester.

Ethanol and ether washed N$^\alpha$-benzyloxycarbonyl-D-2-azetidinylcarbonyl-N$^{im}$-benzyl-L-histidyl-O-benzyl-L-seryl-O-benzyl-L-tyrosyl-D-alanine resin, 13.85 g., is stirred in 50 ml. of dimethylformamide, 20 ml. of triethylamine and 150 ml. of methanol overnight. After filtration and evaporation, the gummy product is solidified with petroleum ether; 3.5 g.; m.p. 75°–149° C. $[\alpha]_D^{23}$ + 10.6° (c. 1.02, dimethylformamide).

N$^\alpha$-Benzyloxycarbonyl-D-2-azetidinylcarbonyl-N$^{im}$-benzyl-L-histidyl-O-benzyl-L-seryl-O-benzyl-L-tyrosyl-D-alanine resin is obtained by the General Procedure given in Example 2 using 10 g. (8 mmol) of N$^\alpha$-t-butoxycarbonyl-D-alanine resin in successive couplings with 1) 3.4 g. (9.14 mmol) of N$^\alpha$-t-butoxycarbonyl-O-benzyl-L-tyrosine and 1.9 g. (9.2 mmol) of dicyclohexylcarbodiimide, 2) 2.8 g. (9.14 mmol) of N$^\alpha$-t-butoxycarbonyl-O-benzyl-L-serine and 1.9 g. of dicyclohexylcarbodiimide, 3) 3.2 g. (9.14 mmol) of N$^\alpha$-t-butoxycarbonyl-N$^{im}$-benzyl-L-histidine and 1.9 g. of dicyclohexylcarbodiimide and 4) 2.2 g. (10 mmol) of N$^\alpha$-benzyloxycarbonyl-D-2-azetidine carboxylic acid and 1.9 g. of dicyclohexylcarbodiimide.

N$^\alpha$-Benzyloxycarbonyl-D-2-azetidinecarboxylic acid is obtained from the known D-2-azetidinecarboxylic acid [Phillips and Cromwell, J. Hetero. Chem., 10, 795 (1973); Rodebaugh and Cromwell, J. Hetero. Chem., 6, 993 (1969)] by reaction with benzyloxycarbonyl chloride and sodium hydroxide.

EXAMPLE 6

N$^\alpha$-t-Butoxycarbonyl-N$^{im}$-benzyl-L-histidyl-L-tryptophyl-O-benzyl-L-seryl-O-benzyl-L-tyrosyl-D-alanine N-ethylamide N$^\alpha$-t-Butoxycarbonyl-N$^{im}$-benzyl-L-histidyl-L-tryptopnyl-O-benzyl-L-seryl-O-benzyl-L-tyrosyl-D-alanine methyl ester, 252 mg., is dissolved in 5 ml. of dimethylformamide and 5 ml. of methanol followed by treatment with 5 ml. of 50% ethylamine in methanol. After 6 days at room temperature, the solution is evaporated and the residue triturated with ether and filtered. The product is dried at 35° C. under reduced pressure; 208 mg.; m.p. 222°–225° C.

The methyl ester is prepared by treating the methanol and ether washed N$^\alpha$-t-butoxycarbonyl-N$^{im}$-benzyl-L-histidyl-L-tryptophyl-O-benzyl-L-seryl-O-benzyl-L-tyrosyl-D-alanine resin with ten percent triethylamine in a mixture of methanol and dimethylformamide overnight, followed by filtration and evaporation. The resin is obtained according to the General Procedure of Example 2 from 15 g. (13.5 mmol) of N$^\alpha$-t-butoxy-carbonyl-D-alanine resin by successive couplings with 1) 6.0 g. (16.2 mmol) of N$^\alpha$-t-butoxycarbonyl-O-benzyl-L-tyrosine and 3.3 g. (16.2 mmol) of dicyclohexylcarbodiimide, 2) 4.8 g. (16.2 mmol) of N$^\alpha$-t-butoxycarbonyl-O-benzyl-L-serine and 3.3 g. of dicyclohexylcarbodiimide, 3) 4.95 g. (16.2 mmol) of N$^\alpha$-t-butoxycarbonyl-L-tryptophan and 3.3 g. of dicyclohexylcarbodiimide and 4) 5.6 g. (16.2 mmol) of N$^\alpha$-t-butoxycarbonyl-N$^{im}$-benzyl-L-histidine and 3.3 g. of dicyclohexylcarbodiimide.

EXAMPLE 7:

N$^\alpha$-Benzyloxycarbonyl-D-2-azetidinylcarbonyl-N$^{im}$-benzyl-L-histidyl-O-benzyl-L-seryl-O-benzyl-L-tyrosyl-D-alanine-N-ethylamide The methyl ester of Example 5, 700 mg., is treated with 30 ml. of methanol and 10 ml. of ethylamine. After evaporation, the crude product is twice precipitated from cooling isopropanol; 490 mg. as a hemihydrate; m.p. 81°–98° C.; $[\alpha]_D^{23}$ −1° (c. 1.04, dimethylformamide).

EXAMPLE 8:

N$^\alpha$-Benzyloxycarbonyl-L-tryptophyl-O-benzyl-L-seryl-O-benzyl-L-tryosyl-D-alanyl-D-leucine methyl ester Ethanol and ether washed N$^\alpha$-benzyloxycarbonyl-L-tryptophyl-O-benzyl-L-seryl-O-benzyl-L-tyrosyl-D-alanyl-D-leucine resin, 10.4 g., is treated overnight with ten percent triethylamine in methanol. After filtration and evaporation, the crude product is precipitated from cooling isopropanol; 1.58 g.; $[\alpha]_D^{23}$ −16.2° (c. 1.01, dimethylformamide).

N$^\alpha$-Benzyloxycarbonyl-L-tryptophyl-O-benzyl-L-seryl-O-benzyl-L-tyrosyl-D-alanyl-D-leucine resin is obtained according to the General Procedure of Example 2 using 53 g. (42.9 mmol) of N$^\alpha$-t-butoxycarbonyl-D-leucine resin in successive couplings with 1) 8.5 g. (45 mmol) of N$^\alpha$-t-butoxycarbonyl-D-alanine and 9.3 g. (45 mmol) of dicyclohexylcarbodiimide, 2) using 44 g. of resin (35.6 mmol) of the 52.8 g. obtained in Step 1, with 13.8 g. (37 mmol) of N$^\alpha$-t-butoxycarbonyl-O-benzyl-L-tyrosine and 7.62 g. (37 mmol) of dicyclohexylcarbodiimide, 3) 11.29 g. (37 mmol) of N$^\alpha$-t-butoxycarbonyl-O-benzyl-L-serine and 7.62 g. of dicyclohexylcarbodiimide and 4) using 10 g. of resin (6.85 mmol) of the 52 g. from Step 3, with 2.83 g. (8 mmol) of N$^\alpha$-benzyloxycarbonyl-L-tryptophan and 1.65 g. (8 mmol) of dicyclohexylcarbodiimide.

N$^\alpha$-t-Butoxycarbonyl-D-leucine resin is obtained from 15.8 g. of N$^\alpha$-t-butoxycarbonyl-L-leucine, 50 g. of chloromethylated resin and 6.5 g. of triethylamine which are stirred together in ethanol for several days, filtered and the resin washed with ethanol, water, methanol, dichloromethane and ether. After drying, the product resin shows 0.757 to 0.807 mmol per g.

EXAMPLE 9:

N$^\alpha$-t-Butoxycarbonyl-N-$^{im}$-benzyl-L-histidyl-L-tryptophyl-O-benzyl-L-seryl-O-benzyl-L-tyrosyl-D-alanine methyl ester N$^\alpha$-t-Butoxycarbonyl-N$^{im}$-benzyl-L-histidyl-L-tryptophyl-O-benzyl-L-seryl-O-benzyl-L-tyrosyl-D-alanine resin is stirred overnight with 250 ml. of methanol, 250 ml. of dimethylformamide and 30 ml. of triethylamine. After filtration and evaporation, the crude ester is a glassy solid which is triturated with ethyl acetate, filtered and washed with ether; 1.48 g.; m.p. 226°–229° C.

EXAMPLE 10:

N$^\alpha$-Benzyloxycarbonyl-L-tryptophyl-O-benzyl-L-seryl-O-benzyl-L-tyrosyl-D-alanyl-D-leucine N-ethylamide The methyl ester of Example 8, 610 mg., is treated at room temperature for several days with 30 ml. of methanol and 10 ml. of ethylamine followed by evaporation, 420 mg.; $[\alpha]_D^{23}$ −28° (c. 0.5, dimethylformamide).

We claim:

1. A pentapeptide of the formula

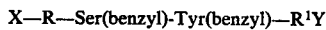

X—R—Ser(benzyl)-Tyr(benzyl)—R$^1$Y wherein X is t-butoxycarbonyl or benzyloxycarbonyl, R is a single amino acid fragment or a dipeptide fragment utilizing amino acids selected from the group consisting of Aze, His(benzyl) and Trp; R$^1$ is a single amino acid fragment or a dipeptide fragment utilizing amino acids selected from the group consisting of Ala, Leu and Pro and Y is lower alkoxy, hydrazino, amino, lower alkylamino and di(lower alkyl)amino with the proviso that the total number of amino acid units when R and R$^1$ are combined is three.

2. The pentapeptides of claim 1 wherein X is t-butoxycarbonyl, R is Trp or His(benzyl), R$^1$ is Ala-Leu or Ala-Pro and Y is methoxy or ethylamino.

3. The pentapeptide of claim 1 having the name N$^\alpha$-t-butoxycarbonyl-D-tryptophyl-O-benzyl-L-seryl-O-benzyl-L-tyrosyl-D-alanyl-L-leucine methyl ester.

4. The pentapeptide of claim 1 having the name N$^\alpha$-t-butoxycarbonyl-D-tryptophyl-O-benzyl-L-seryl-O-benzyl-L-tyrosyl-D-alanyl-D-proline N-ethylamide.

5. The pentapeptide of claim 1 having the name N$^\alpha$-t-butoxycarbonyl-D-tryptophyl-O-benzyl-L-seryl-O-benzyl-L-tyrosyl-D-alanyl-L-proline N-ethylamide.

6. The pentapeptide of claim 1 having the name N$^\alpha$-t-butoxycarbonyl-N$^{im}$-benzyl-L-histidyl-O-benzyl-L-seryl-O-benzyl-L-tyrosyl-D-alanyl-L-leucine methyl ester.

7. The pentapeptide of claim 1 having the name N$^\alpha$-t-butoxycarbonyl-N$^{im}$-benzyl-L-histidyl-O-benzyl-L-seryl-O-benzyl-L-tyrosyl-D-alanyl-L-leucyl hydrazide.

* * * * *